United States Patent [19]

Domb

[11] Patent Number: 5,171,812

[45] Date of Patent: Dec. 15, 1992

[54] POLYANHYDRIDES OF OLIGOMERIZED UNSATURATED ALIPHATIC ACIDS

[75] Inventor: Abraham J. Domb, Baltimore, Md.

[73] Assignee: Nova Pharmaceutical Corporation, Baltimore, Md.

[21] Appl. No.: 467,635

[22] Filed: Jan. 19, 1990

[51] Int. Cl.$^5$ .............................................. C08F 22/04
[52] U.S. Cl. ................................. 526/318.2; 528/206; 528/271
[58] Field of Search ....................... 526/318.2; 528/271, 528/206

[56] References Cited

U.S. PATENT DOCUMENTS

| | | |
|---|---|---|
| 4,757,128 | 7/1988 | Domb et al. |
| 4,789,724 | 12/1988 | Domb et al. |
| 4,857,311 | 8/1989 | Domb et al. |
| 4,886,870 | 12/1989 | D'Amore et al. |
| 4,888,176 | 12/1989 | Langer et al. |
| 4,891,225 | 1/1990 | Langer et al. |

OTHER PUBLICATIONS

Leong, et al., *J. Med. Biomed. Mater. Res.* 19, 941 (1985).

Leong, et al., *J. Med. Biomed. Mater. Res.* 20, 51 (1986).

Rosen, et al., *Biomaterials* 4, 131 (1983).

*Primary Examiner*—Joseph L. Schofer
*Assistant Examiner*—N. Sarafin
*Attorney, Agent, or Firm*—Kilpatrick & Cody

[57] ABSTRACT

A polyanhydride suitable for use as a matrix material in controlled delivery devices polymerized from monomers of the general formula:

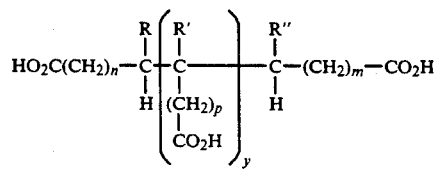

wherein R, R', and R" are the same or a different aliphatic chain of $C_1$ to $C_{20}$ or hydrogen; m, n, and p are integers from 0 and 20; y is 0 or 1; and, if y is 0, one of R or R' is not H.

13 Claims, 2 Drawing Sheets

POLYANHYDRIDES OF OLIGOMERIZED UNSATURATED ALIPHATIC ACIDS

BACKGROUND OF THE INVENTION

This invention is in the area of polymers for controlled delivery of substances, and is specifically a polyanhydride prepared from oligomerized unsaturated aliphatic acids.

There has been extensive research in the area of biodegradable controlled release systems for bioactive compounds. Biodegradable, biocompatible matrices for drug delivery are useful because they obviate the need to remove the drug-depleted device.

The most desirable polymeric matrix for drug delivery is one that is hydrophobic, stable, strong, flexible, soluble in organic solution, has a low melting point, and degrades linearly over time. The polymer must be hydrophobic so that it retains its integrity for a sufficient time when placed in an aqueous environment, such as the body, to effect controlled release. The polymer must be stable to storage for an extended period before use. The polymer must be strong, yet flexible enough that it does not crumble or fragment during use.

Controlled release devices are typically prepared in one of several ways. In one method, the polymer is melted, mixed with the substance to be delivered, and then cooled. Melt fabrication requires that the polymer have a melting point that is below the temperature at which the substance to be delivered and polymer degrade or become reactive. Alternatively, the device can be prepared by solvent casting, in which the polymer is dissolved in a solvent, and then the substance to be delivered is dissolved or dispersed in the solution. The solvent is then evaporated, leaving the substance in the polymeric matrix. Solvent casting requires that the polymer be soluble in organic solvents.

For controlled drug delivery, the polymer must degrade by surface erosion and not by bulk erosion. Surface erosion occurs when the rate of hydrolytic degradation on the surface of the polymeric structure is faster than the rate of degradation in the interior of the polymeric structure. Bulk erosion occurs when the polymer incorporates water into the center of the matrix, rendering the polymer sponge-like with hole, or channels in the matrix. When bulk erosion occurs, the material to be delivered is released through the channels in a rapid, uncontrolled fashion.

Many polymers have been evaluated for use as controlled drug delivery matrices, including polyesters, polyamides, polyurethanes, polyorthoesters, polyacrylonitriles, and polyphosphazenes. None of these polymers have exhibited the desired combination of characteristics for use in the controlled delivery of substances.

Polyanhydrides have also been studied for use in controlled delivery devices. See, for example, U.S. Pat. No. 4,891,225 to Langer, et al., U.S. Pat. No. 4,886,870 to D'Amore, et al., Leong, et al., *J. Med. Biomed. Mater. Res.* 19, 941 (1985); and Leong, et al., *J. Med. Biomed. Mater. Res.* 20, 51 (1986). One of the first polyanhydrides studied with respect to controlled release characteristics was poly(bis(p-carboxyphenoxy)methane anhydride), as described by Rosen, et al., *Biomaterials* 4, 131 (1983). The aromatic polyanhydride exhibited near zero order (linear) erosion and release kinetics at 37° C. and 60° C., in vitro.

Shortly thereafter, three related polyanhydrides, poly 1,3-(bis(p-carbophenoxy)propane anhydride (p-CPP) (an aromatic polyanhydride), the polymer formed from the copolymerization of CPP with sebacic acid (a copolymer of an aromatic diacid and an aliphatic diacid), and polyterephthalic acid (an aromatic anhydride) were prepared and studied, as described by Leong, et al., *J. Med. Biomed. Mater. Res.* 19, 941 (1985).

It was found that aromatic polyanhydrides have unacceptably long degradation rates. For example, it was estimated that a delivery device prepared from p-CPP would require more than three years to completely degrade in vivo. Further, anhydride homopolymers of aromatic or linear aliphatic dicarboxylic acids were found to be highly crystalline and have poor film forming properties. Aromatic polyanhydrides also have high melting points and low solubility in organic solvents.

As described in U.S. Pat. No. 4,757,128 to Domb and Langer, high molecular weight copolymers of aliphatic dicarboxylic acids with aromatic diacids are less crystalline than aromatic or linear aliphatic polyanhydrides, and they form flexible films.

Degradation rates are also increased by copolymerizing an aromatic dicarboxylic acid with an aliphatic diacid; however, bulk erosion occurs because areas of the polymer containing aliphatic anhydride linkages erode faster than aromatic anhydride linkages, leaving channels in the matrix through which the substance to be delivered is released in an uncontrolled fashion. For example, in the p-CPP sebacic acid copolymer, the aliphatic anhydride bonds are cleaved and all drug released in ten days, while the aromatic regions remained intact for over five months. Further, the copolymers have inferior mechanical properties; they become brittle and crumble into flakes on exposure to moisture.

Polymers prepared from linear aliphatic diacids are hydrophilic solids that degrade by bulk erosion, resulting in a rapid release of the drug from the polymeric matrix. Hydrophobicity is increased by copolymerizing the linear aliphatic diacids with aromatic diacids, however this approach results in an increase in the polymer melting temperature and a decrease in organic solvent solubility. Furthermore, it does not improve the drug release profile but increases the degradation and the elimination time of the polymer both in vivo and in vitro. Since both homopolymers and copolymers of linear aliphatic diacids are very sensitive to moisture, they require extremely anhydrous and low temperature storage conditions.

Several attempts have been made to improve the controlled release characteristics of polyanhydrides by altering the method of synthesis or the molecular weight. See, for example, U.S. Pat. No. 4,857,311 to Domb and Langer, describing polyanhydrides with a uniform distribution of aliphatic and aromatic residues in the chain, prepared by polymerizing a dicarboxylic acid with an aromatic end and an aliphatic end; U.S. Pat. No. 4,888,176 to Langer, et al., describing the preparation of high molecular weight polyanhydride controlled delivery devices; and U.S. Pat. No. 4,789,724 to Domb and Langer describing the preparation of very pure anhydride copolymers of aromatic and aliphatic diacids.

There remains is a strong need for a polymer having the desired characteristics of hydrophobicity, stability, strength, flexibility, organic solubility, low melting point, and appropriate degradation profile, for use as the matrix for a controlled delivery device.

It is therefore an object of the present invention to provide a biodegradable polymer that is highly hydrophobic, and that degrades by surface erosion to release an incorporated substance in a controlled manner.

It is another object of the present invention to provide a polymer that is thermodynamically and hydrolytically stable and that requires mild storage conditions.

It is yet another object of the present invention to provide a strong and flexible polymer film that degrades in vivo into a soft material that can be gradually eliminated from the body.

It is a further object of the present invention to provide a controlled delivery device that is suitable for intraperitoneal implantation.

SUMMARY OF THE INVENTION

The present invention is a polyanhydride suitable for use as a matrix material in controlled delivery devices. The polyanhydride is synthesized from monomers prepared by linking two or more unsaturated aliphatic carboxylic acids to form a non-linear aliphatic di- or polyorganic acid of the general formula:

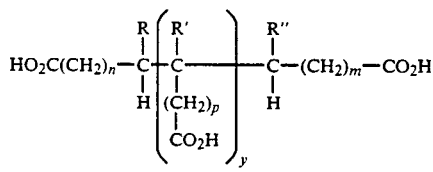

wherein R, R', and R" are the same or different aliphatic chain of $C_1$ to $C_{20}$ or hydrogen; m, n, and p are integers from 0 and 20; y is 0 or 1; and, if y is 0, one of R or R' is not H.

Suitable monomers include the dimers and trimers of naturally occurring unsaturated fatty acids or non-naturally occurring unsaturated carboxylic acids. Naturally occurring and synthetic unsaturated acids can also be coupled to form a mixed oligomer that is polymerized. The oligomerized monomer is typically a hydrophobic liquid.

Films made from these polymers are highly flexible (can be bent 180° at room temperature without breaking) and strong (between 1-20 megaPascal), yet degrade into a soft film that gradually disappears without forming harmful sharp flakes. The polymers are soluble in organic solvents and have melting points in the range of 25° to 65° C. The polymers degrade without significant bulk erosion over a period of days. The polymers release incorporated substance at a rate corresponding to their degradation rate (zero order release).

DETAILED DESCRIPTION OF THE INVENTION

Figure 1:
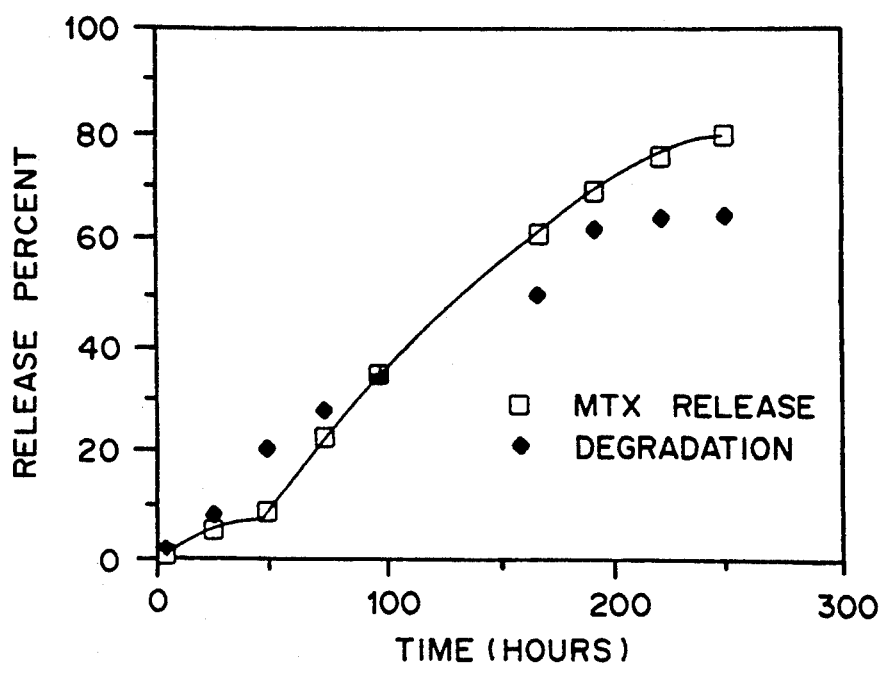
FIG. 1 is a graph comparing the percent release of methotrexate (MTX) from poly(FAD-SA) (6:4, weight/weight) over time (hours) in phosphate buffer, pH 7.4, at 37° C.

The disclosed invention is a polyanhydride suitable for use as a matrix material in controlled delivery devices. The polyanhydride is prepared from oligomerized, unsaturated, naturally occurring or synthetic aliphatic organic acids. The monomers ar prepared by linking two or more unsaturated aliphatic carboxylic acids to form a non-linear aliphatic di- or polyorganic acid of the general formula:

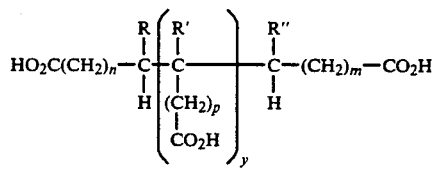

wherein R, R', and R" are the same or a different aliphatic chain of $C_1$ to $C_{20}$ or hydrogen; m, n, and p are integers from 0 and 20; y is 0 or 1; and, if y is 0, one of R or R' is not H.

If the polymer is used for medical applications, monomers should be chosen that are biocompatible and biodegradable. Suitable monomer include the dimers and trimers of naturally occurring unsaturated fatty acids, such as oleic, erucic, lauroleic, myristoleic, gadoleic, ricinoleic, palmitoleic, linoleic, linolenic, and arachidonic acids. These fatty acid derivatives should be readily eliminated from the body through the normal metabolic pathways for fatty acids.

Diacids or triacids can also be synthesized from non-naturally occurring carboxylic acids, such as acrylic, methacrylic, fumaric, crotonic, vinyl acetic (3-butenoic), isocrotonic, allylacetic (4-pentenoic), hexenoic and undecylenic acids. Naturally occurring and synthetic unsaturated acids can be coupled to form a mixed oligomer. The oligomerized monomers are typically hydrophobic liquids.

Dimers and trimers of oleic acid are available from commercial sources. Unichema Chemicals, Inc. (Chicago, Ill.) sells the dimer as Pripol 1009 (99% diacids; molecular weight 556). It sells the trimer as Pripol 1025 (containing 25% by weight of trimer and 75% dimer) and Pripol 1040 (78% trimer and 22% dimer). Henkel Corporation (LaGrange, Ill.) sells the following oligomerized oleic acid monomers: Versadyme 213 (50-70% trimer, 25-40% dimer); Versadyme 288, 58, and 52 (97% dimer); Versadyme 204 (83% dimer, 17% monomer); and Versadyme 216 and 228 (88% dimer).

The oligomerized unsaturated carboxylic acid monomers can also be synthesized from the corresponding unsaturated acids by methods known to those skilled in the art. See for example *Advanced Organic Chemistry* J. March, editor, 3 ed., John Wiley & Sons, New York, New York 1985.

Oligomerized unsaturated aliphatic acids can be polymerized by methods known in the art, including melt polycondensation and solution polymerization. In the method of melt polycondensation, described by Domb, et al., in *J. Poly. Sci* 25, 3373 (1987), a prepolymer is prepared by heating the diacid with acetic anhydride to form a diacetyldianhydride. The prepolymer is then heated neat under vacuum to form the polymer. Mixtures of diacetyldianhydrides can also be polymerized with this method.

Solution polymerization is described in U.S. patent application Ser. No. 07/269,448, filed on Jul. 31, 1987, by Domb et al., entitled "One Step Polymerization of Polyanhydrides," now allowed, the teachings of which are incorporated herein. Solution polymerization involves the coupling of diacids with phosgene in an organic solvent. Poly(4-vinylpyridine) is added to remove the HCl from solution. For example, diphosgene (0.5 equivalents) is added dropwise to a stirred mixture of diacid (1.0 equivalent) and poly(4-vinylpyridine) (2.5 equivalents) in 20 ml of chloroform. The solution is stirred for 3 hours at 25° C. The insoluble PVP.HCl is removed by filtration. The solvent is then removed and the precipitate is isolated, washed with ethyl ether, and then dried at 25° C. for 24 hours in a vacuum oven.

The physical properties of the polyanhydride are often improved by copolymerizing the oligomerized unsaturated aliphatic acid with another dicarboxylic acid, for example, sebacic acid (SA), isophthalic acid (ISO), adipic acid (AA), 1,10-dodecanoic acid (DD), or 1,3 bis(p-carboxyphenoxypropane) (CPP).

Biodegradable biocompatible polyanhydride films prepared as described herein can be used as a physical barrier for adhesion prevention using the method of Linsky, et al., *J. Reprod. Med.* 32, 17 (1987)); or for targeted release of drugs to specific organ surfaces. Examples are films containing heparin for the prevention of blood clotting, and films releasing dexamethasone or cyclosporin to prevent organ transplant rejection. Biodegradable films can also be used in guided tissue regeneration in periodontal disease using the method reported by Nyman et al., *J. Clin. Perio.* 9, 290 (1982); Nyman et al., *J. Clin. Perio.* 13, 604 (1986); Nyman et al., *J. Clin. Perio.* 14, 618 (1987), Nyman et al., *J. Clin Perio.* 15, 288 (1988), or as tubes for guided nerve regeneration using the method of U.S. Pat. No. 4,870,966 to Dellon L. and Mackinnon S. E.

Other medical applications for the polyanhydride films described here including coatings for implantable devices, i.e. stents, catheters, artificial vascular grafts, and pacemakers. The coating can incorporate antibiotics, anti-inflammatories, or anti-clotting agents for release at a predetermined rate, to decrease complications caused by the implanted devices. Controlled delivery devices prepared from these polyanhydrides can also be used as ocular inserts for extended release of drugs to the eye.

The polyanhydrides of the present invention are described in greater detail in the following non-limiting working examples using dimers and trimers of oleic acid, a naturally occurring fatty acid, for ease of illustration.

Oleic acid dimer (referred to below as FAD) and trimer (referred to below as FAT) were obtained from Unichema Chemicals, Inc. (Pripol 1009 and Pripol 1025, respectively). Both are liquids at room temperature.

Infrared spectroscopy was performed on a Perkin-Elmer 1310 spectrophotometer (Perkin-Elmer, CT.). Polymeric samples were film cast onto NaCl plates from a solution of the polymer in chloroform. Acids and prepolymer samples were either pressed into KBr pellets or dispersed in nujol onto NaCl plates. A Perkin Elmer DSC 7 Differential Scanning Calorimeter calibrated with indium was used to determine the glass transition temperature (Tg), the melting temperature (Tm), and the heat of fusion of the polymers. The standard heating rate for all polymers was 10° C./min, under nitrogen atmosphere. The decomposition temperatures were determined on a Dupont 951 Thermogravimetric Analyzer (TGA) at a heating rate of 20° C./min. in a nitrogen atmosphere. The molecular weights of the polymers were estimated on a Waters GPC system (Waters, MA) consisting of a Waters 510 pump and Waters programmable multiwavelength detector at 254 nm wavelength. Samples were eluted in dichloromethane through two Styrogel(TM) columns (Waters, Linear and a $10^4$ A pore sizes) in series at a flow rate of 1.0 mL/min. Molecular weights of polymers were determined relative to polystyrene standards (Polysciences, P.A., molecular weight range, 400 to 1,500,000) using Maxima 840 computer programs (Waters, M. A.). $^1$H NMR spectra were obtained on a Varian 250 MHz spectrophotometer using deuterated chloroform containing tetramethylsilane (TMS) as the solvent for the polymers and prepolymers. UV absorbencies were determined on a Lambda 3B spectrophotometer (Perkin Elmer, CT). Degradation studies were performed at 37° C., using melt molded or film cast samples containing drug placed in a 200 ml solution of phosphate buffer at pH 7.40. The release of drug to the medium was determined by the UV absorption or HPLC (high pressure liquid chromatography) of the drug.

EXAMPLE 1

Preparation of Prepolymers of Oligomerized Oleic Acid.

The fatty acid FAD and FAT oligomers were separately purified by extraction of a dichloromethane solution of the oligomer (50% w/v) with deionized water. The purified monomers were then separately refluxed in acetic anhydride (100 g in 500 ml) for one hour and evaporated to dryness.

The infrared spectra for both prepolymers included the following absorbances: (cm-1, film cast) 1800, 1740 (sharp). The proton NMR for the prepolymers contained the following chemical shifts: 0.9(m,6H), 1.3(s,52H), 1.7(m,2H), 2.2(s,4H), 2.4(m,4H).

Prepolymers of sebacic acid, isophthalic acid, adipic acid, 1,10-dodecanoic acid, and 1,3 bis(p-carboxyphenoxypropane) were prepared as described by A. Domb and R. Langer in *J. Polym. Sci.* 25, 3373 (1987).

EXAMPLE 2

Polymerization of the Prepolymers

Polymers of varying combinations of oligomers and aliphatic diacids were synthesized by melt polycondensation of diacetyldianhydride prepolymers or by solution polymerization of the diacids.

The melting point, molecular weight, and appearance of the polyanhydrides prepared by melt polycondensation are provided in Table I. The melting point, molecular weight, and appearance of polyanhydrides prepared by solution polymerization are provided in Table 2. The ratio of monomers was calculated on a weight/weight basis. The following abbreviations are used in the tables: SA, sebacic acid; CPP, 1,3-bis(p-carboxyphenoxy)propane; DD, 1, 10-dodecanoic acid; and ISO, isophthalic acid.

Polyanhydrides prepared according to this method have low melting temperatures, in the range of 25° C. to 65° C., and high solubility in chloroform, dichloromethane, tetrahydrofuran, ethyl acetate and methyl ethyl ketone. These characteristics allow the polymer to be easily fabricated into controlled delivery devices. High molecular weight polymers, in the range of 18,300 to 243,100, were obtained by melt polymerization.

All polymers displayed the typical IR absorbances for aliphatic polyanhydrides (2910, 2860, 1810, and 1750 cm$^{-1}$). Copolymers containing an aromatic unit or fumaric acid had an additional sharp peak at 1600 cm$^{-1}$. The H-NMR spectra of the polymers were consistent with their polymeric structures.

None of the polyanhydrides prepared had a glass transition temperature (Tg) in the temperature range of $-50°$ to $+50°$ C. In addition, all had a low heat of fusion (<5 Jouls/gram), indicating low crystallinity (<5%). P(FAD-SA) (50:50) and P(FAD-DD) (50:50) decomposed at 292° C. and 296° C., respectively.

TABLE 1

Analysis of Polyanhydrides Prepared by Melt Condensation.

| Polymer | Melting Point (°C.) | Molecular Weight Mn | Mw | Physical Appearance |
|---|---|---|---|---|
| P(FAD) | 25–35 | 18,600 | 88,700 | soft clear sticky |
| P(FAD-SA)50:50 | 60–65 | 18,200 | 243,100 | clear flexible |
| P(FAD-SA)33:66 | 42–47 | 16,900 | 175,200 | soft clear rubbery |
| P(FAD-CPP) 50:50 | 35–40 | 8,900 | 18,300 | sticky soft white |
| P(FAD-CPP) 80:20 | 30–35 | 9,100 | 23,600 | sticky soft white |
| P(FAD-ISO)50:50 | 38–42 | 15,700 | 48,800 | sticky clear soft |
| P(FAD-SA-CPP) 45:45:10 | 55–60 | 10,300 | 86,200 | strong flexible |
| P(FAD-DD)50:50 | 38–42 | 20,100 | 123,700 | clear flexible |
| P(FAD-AA)50:50 | 25–30 | 9,300 | 24,600 | sticky clear semisolid |
| P(FAD-FA)50:50 | 25–30 | 10,400 | 26,300 | sticky dark semisolid |
| P(FAT) | a | insoluble | insoluble | clear rubbery |
| P(FAT-SA)50:50 | 58–63 | 15,300 | 85,900 | flexible hard solid |
| P(FAT-SA)33:66 | 56–60 | 11,200 | 74,700 | flexible hard solid |
| P(FAT-CPP) 50:50 | a | insoluble | insoluble | rubbery |
| P(FAT-CPP) 80:20 | a | insoluble | insoluble | rubbery |
| P(FAT-SA-CPP) 40:50:10 | 54–58 | 10,700 | 55,700 | flexible hard solid |
| P(FAT-SA-CPP) 40:40:20 | 61–64 | 10,400 | 53,700 | flexible hard rubber |
| P(FAT-FAD-SA) 3:1:1 | 41–44 | 15,700 | 88,800 | sticky hard rubber |
| P(FAT-DD)50:50 | 41–45 | 8,500 | 35,200 | soft breakable rubbery- | a melting temperature in excess of 200° C.

TABLE 2

Analysis of Polyanhydrides Prepared by Solution Condensation[a].

| Polymer | Melting Point (°C.) | Molecular Weight Mn | Mw | Physical Appearance |
|---|---|---|---|---|
| P(FAD) | 25–35 | 5,600 | 13,400 | soft clear sticky |
| P(FAD-SA) 50:50 | 60–65 | 8,600 | 24,300 | soft flexible |
| P(FAD-SA-CPP) 45:45:10 | 52–60 | 6,700 | 17,400 | strong flexible |
| P(FAD-DD) 50:50 | 38–42 | 7,900 | 26,500 | clear flexible |

[a]The polymers were synthesized in dichloromethane solution using phosgene as coupling agent and pyridine as an acid acceptor.

EXAMPLE 3

Preparation of Polyanhydride Films

Polyanhydride films were prepared by melt or solvent casting using the following methods.

Solvent casting

The polyanhydrides were dissolved in dichloromethane (1 g dissolved in 5 ml) and cast on a Teflon(TM) coated Petri dish. When drug was incorporated into the film, the drug powder was dissolved or dispersed in the polymer solution prior to casting. On solvent evaporation, transparent strong films were obtained from most of the polymer compositions described in Table 1.

Melt Casting

200 Milligrams of polymer were compressed between two hot plates heated to the melting point of the compressed polymer. Partially crosslinked polymers based on trimer fatty acids prepared from Pripol 1025 (Example 2, polymers 12–19) formed flexible and strong films using the melt technique.

Polyanhydride films prepared as described above are useful as laminates for degradable or nondegradable fabrics. FAD-SA copolymers are particularly useful for this purpose. As an example, poly(FAD-SA) (50:50) was laminated onto a biodegradable oxidized cellulose (Surgicell TM) by solvent casting or melt compression (0.5 gram on 2 gram of fabric) to form a solid nonporous sheet. The sheet can be used as a degradable physical barrier for adhesion prevention.

EXAMPLE 4

Release of Methotrexate (MTX) from Polyanhydrides.

Figure 2:
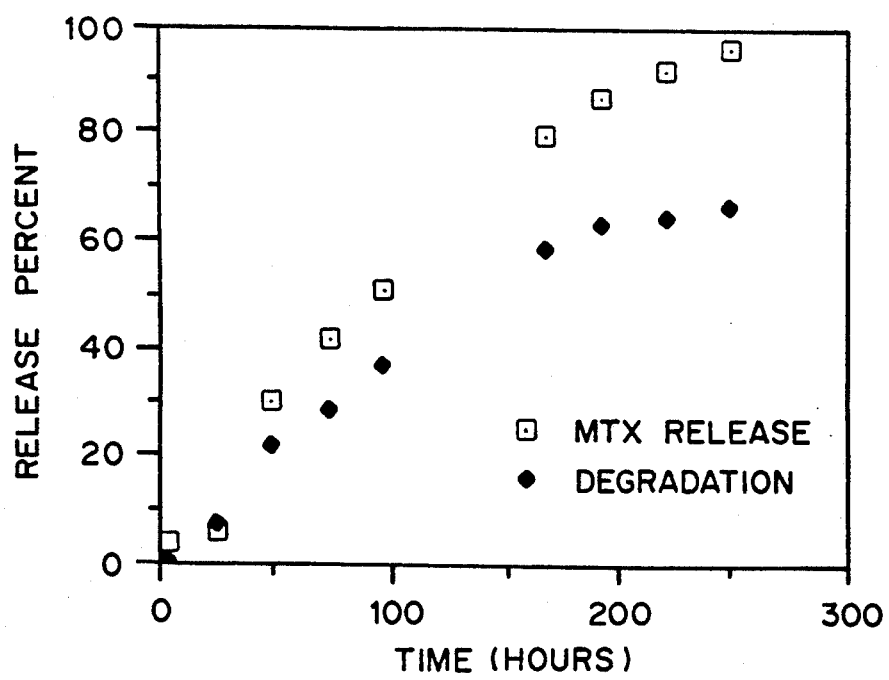
FIG. 2 is a graph comparing the percent release of methotrexate from poly(FAT-SA) (6:4, weight/weight) over time (hours) in phosphate buffer, pH 7.4, at 37° C.

Methotrexate (MTX; 100 mg) was uniformly dispersed in a molten sample of poly(FAD-SA) (6:4) weight/weight) (0.9 g) and separately in a molten sample of poly(FAT-SA) (6:4 weight/weight) (0.9 g). The samples were cast to tough yellow slabs (6×10×1 mm, about 200 mg). The in vitro release of methotrexate from the polyanhydride was determined in phosphate buffer (pH 7.4) at 37° C. by HPLC analysis (C18 column, mobile phase: ammonium persulphate pH 3.5, 1 ml/min). The rate of release of MTX from poly(FAD-SA) (6:4) and poly(FAT-SA) (6:4) as well as the degradation rates of the polymers, are illustrated in FIGS. 1 and 2, respectively.

As shown, MTX is released from the polymers at a linear rate approximately corresponding to the degradation rates of the polymers. Over 80% of the drug was released from poly(FAD-SA) (6:4) in 250 hours, and over 95% of the drug was released from poly(FAT-SA) (6:4) in the same time period.

EXAMPLE 5

Release of Gentamicin from Polyanhydrides.

Figure 3:
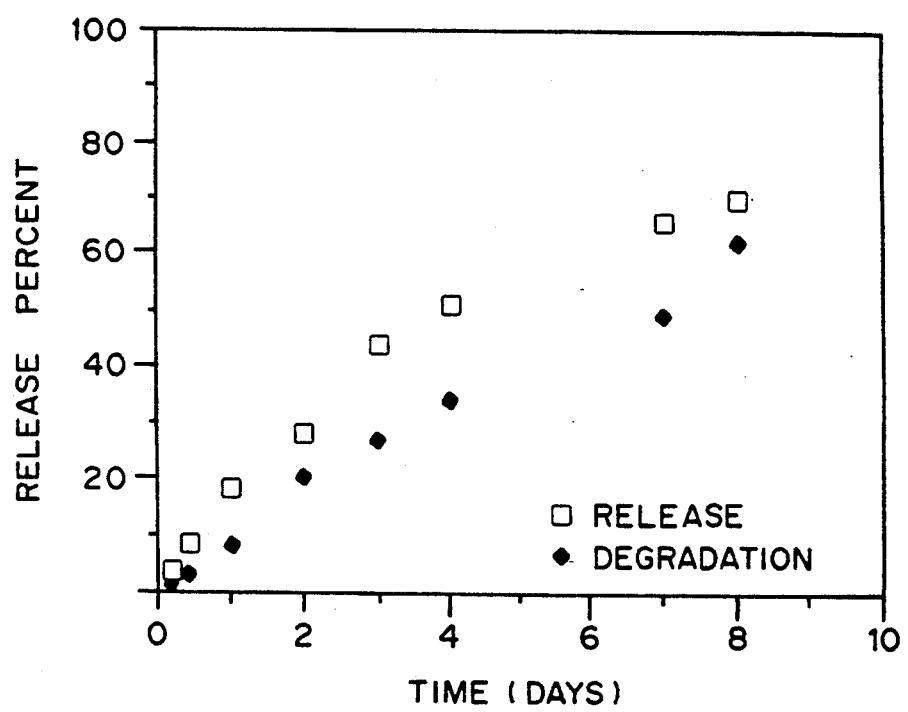
FIG. 3 is a graph comparing the percent release of gentamicin from poly(FAD-SA) (6:4, weight/weight) over time (hours) in phosphate buffer, pH 7.4, at 37° C.

Gentamicin sulphate (200 mg) was uniformly distributed in a molten sample of poly(FAD-SA) (1:1) (1.8 g). The sample was cast to tough but flexible off-white rods (3×25 mm). The rods were cut into 200 mg samples. The in vitro release of gentamicin was determined in phosphate buffer at pH 7.4 and 37° C, by radioimmunoassay (RIA). The degradation rate of the polymer was determined from the weight loss of the sample. The rate of release of gentamicin from poly(FAD-SA) (1:1) as well as the degradation rate of the polymers is illustrated in FIG. 3.

As shown, gentamicin was consistently released from the polyanhydride over a period of approximately 10 days. After 15 days, the polymer was completely degraded, leaving the water insoluble FAD as a semi-liquid mass.

To investigate whether the polymer was eroding predominately from the surface, at various time intervals, polymer samples were removed from the gentamicin containing slab and cut in the middle for observation. The samples were found to have a solid core, containing anhydride bonds, that decreased in size with time, leaving a soft shale of the FAD degradation products (as determined by IR and H-NMR spectroscopy) indicative of surface erosion.

EXAMPLE 6

Release of Cisplatin and Carboplatin from Polymers.

Poly(FAD-SA) (50:50) samples containing the anticancer agent Cisplatin or Carboplatin (3 mg in a 30 mg circular tablet, 3×3 mm) were prepared by melt casting. The in vitro release rates were determined as described in Example 5. The release of drug was monitored by atomic absorption spectroscopy. The drugs were released at a linear rate approximately corresponding to the degradation rates of the polymers, over a period of 14 days.

EXAMPLE 7

Films containing Heparin.

Heparin containing films were prepared by mixing heparin powder (121 units/mg, particle size less than 65 microns) into molten polymer (300 mg, Poly(FAD:SA) (1:1) weight/weight) and then melt pressing the mixture to form films (0.1 mm thick and 12 cm² wide) containing 2, 5, 10, and 15 units per mg of film. The mechanical properties of the film, i.e., flexibility and strength, were not affected by drug incorporation.

The release of heparin from these films was determined in vitro by immersing a film sample in 0.1M phosphate buffer at pH 7.4. The amount of heparin released into the buffer was determined by increasing inhibition of blood clotting. Thirty percent of the heparin was released from films containing 5 units/mg in one hour; 55% was released in six hours; 78% in 18 hours; 85% in 24 hours and 100% in 48 hours. No drug remained in the polymer after 48 hours.

The rate of release of heparin from the films can be manipulated by compressing heparin loaded films between two drug free films or by varying the drug concentration or thickness of the film. Films that release heparin over a period of 4 days were obtained using these methods.

To obtain drug release from one side of the film only, the drug loaded film was compressed with a drug free film on one side. These films were effective in vivo to prevent adhesions and clotting prevention.

EXAMPLE 8

Hydrolytic Stability of Polyanhydride Films

The hydrolytic stability of the polyanhydride films (0.1 mm thickness) were tested by storing the polymers at 25° C. under 70% relative humidity, and monitoring the changes in the film properties over time. The results are summarized in Table 3.

Polyanhydrides of fatty acid oligomers (films 5-11) are flexible and strong when prepared, and remain flexible and relatively strong after 5 days at room temperature exposed to air. For comparison, under similar conditions, films of linear aliphatic homopolymers and copolymers with aromatic diacids became brittle and fragmented after 24 hours.

Polymers prepared from fatty acid oligomers remained stable when stored in an aluminum foil pouch under dry argon at 5° C. for at least 2 months.

TABLE 3

Stability of polyanhydride films.

| Polymer | film properties after | | | |
|---|---|---|---|---|
| | 1 hr | 24 hr | 48 hr | 5 days |
| P(CPP-SA)1:4 | flexible | brittle, fragmented | fragmented to white flakes | fragmented to small fragments |
| P(CPP-SA)1:1 | flexible | brittle, fragmented when bending | fragmented | fragmented to small fragments |
| P(SA) | brittle | brittle, fragmented | fragmented to small fragments | small fragments |
| P(DD) | less brittle than P(SA) | brittle, fragmented | fragmented small fragments | small fragments |
| P(SA-Iso)1:4 | flexible | brittle, fragmented | fragmented to white flakes | fragmented to small fragments |
| P(FAD-SA)1:1 | flexible strong | flexible, clear | flexible, clear | flexible, weak |
| P(FAT-SA)1:1 | flexible strong | flexible strong | flexible, clear | flexible, weak |
| P(FAT-CPP-SA) 4:0:5:4 | flexible strong | flexible strong | flexible, strong | flexible, weak |
| P(FAS-DD)1:1 | flexible strong | flexible, clear | flexible, clear | flexible, weak |
| P(FAT-DD)1:1 | flexible strong | flexible strong | flexible, clear | flexible, weak |
| P(FAT-DD)1:2 | flexible strong | flexible, clear | flexible, clear | flexible, weak |

EXAMPLE 9

Degradation of Polyanhydrides in Buffer Solutions.

The hydrolytic degradation characteristics of polyanhydrides described in Table 3 were evaluated by immersing the films in buffer at pH 7.4 and 37° C., and monitoring the physical properties of the polymers over time.

Polyanhydrides prepared from oligomerized fatty acids (films 6-11) did not fragment after 5 days in buffer. At day one, the films were as flexible as at time zero, and they were relatively strong. After 2 days the films were still flexible and strong enough to be handled. After 5 days the films became weak and soft, and when mixed with a spatula formed a soft semi-solid mass.

In contrast, the films of linear aliphatic homopolymers and copolymers with aromatic diacids (films 1-5) became white and rigid after 1 day, and crumbled into sharp small flakes after two days.

EXAMPLE 10

Biocompatibility studies.

Twelve female Sprague-Dawley rats (250-300 gram weight, 8-14 weeks of age) were implanted with 200 mg melt molded polymer discs (1 mm thick; poly(FAD-SA) (1:1), poly(FAD-SA-CPP) (5:4:1), and clinical grade poly(CPP-SA) (20:80)) using the following procedure. After prepping and draping the rat under sterile conditions, an 8 cm midline incision was made on the dorsum. Using fine tissue scissors, a pocket area was created 6 cm away from the midline incision. One 200 mg disc or no disc was implanted, and the wound was then closed using surgical clips. Seven days after implantation, the rats were sacrificed and the site of implantation was examined.

In Group 1 (control animals), 3/3 sites were found to be normal, with no swelling or redness. In Group 2 (poly(FAD-SA) (1:1) disc), 3/3 sites were also normal. Most of the film material remained in the site of implantation as a waxy semi-solid. In Group 3 (poly(FAD-SA-CPP) (5:4:1) discs), ⅔ sites were normal, and one site showed some red foci. In Group 4 (poly(CPP-SA) (20:80) disc), 2/3 sites were normal, and one site had red foci.

Both poly(FAD-SA) (1:1) and poly(FAD-SA-CPP) (5:4:1) copolymers displayed similar or better biocompatibility than the reference biocompatible polymer, poly(CPP-SA) (20:80).

EXAMPLE 11

Intraperitoneal Implantation of the Polyanhydrides.

Films ($1 \times 1$ cm$^2$, 0.12 mm) of poly(FAD-SA) (1:1), poly(FAD-SA-CPP) (5:4:1), and clinical grade poly(CPP-SA) (20:80) as reference, were implanted into the peritoneal cavity of rats as described in example 10. Animals were sacrificed and examined after one or five weeks. After one week, the reference films (poly(CPP-SA) (20:80)) had completely crumbled to white flakes and had spread out in the peritoneal cavity. In contrast, the fatty acid based films remained as soft materials somewhat stuck to the surface of the organ they had been placed. The site of implantation was clean with no tissue response, indicating that the polymers were highly biocompatible.

The animals sacrificed after five weeks showed no inflammation at the site of implantation. Further, most of the polymer had disappeared by this time.

EXAMPLE 12

Tensile Strength of polymer films.

The tensile strength of solvent casted or melt compressed films of polymers prepared as in Example 2 (numbers 2, 7, 8, 12, and 16) were tested. The results are provided in Table 4.

Solvent casted films were prepared from 10% w/v solutions in dichloromethane at room temperature. After drying the films were stored under vacuum for 12 hours.

Alternatively, polymer samples (200 mg) were compressed between two Teflon ™ coated hot plates to form films using a Carver laboratory press. Tensile measurements were made using an Instron Tensile Tester Model 1122 at room temperature according to ASTM D882-83. Tensile strength, tensile modulus, elongation at yield and break were determined. The tensile values were calculated from the arithmetic average of at least four measurements obtained from four separate specimens per polymer sample.

As seen in Table 4, films made by melt compression are stronger than films prepared by solvent casting. All films were transparent and very flexible. Adding a trifunctional monomer (FAT) almost doubled the tensile strength of the films. Additional increase in the tensile strength can be achieved by incorporating small amounts of an aromatic monomer (CPP) in the polymer.

TABLE 4

Mechanical Properties of Fatty Acid Polyanhydride Films

| Polymer | Method[a] | Tensile Strength (MPa) | Tensile Modulus (MPa) | Elongation yield (%) | Elongation break (%) |
|---|---|---|---|---|---|
| 1-2.P(FAD-SA) | A | 4 | 45 | 14 | 85 |
| 1-2.P(FAD-SA) 50:50 | B | 3 | 35 | 18 | 115 |
| 1-7.P(FAD-DD) 50:50 | A | 5 | 50 | 13 | 77 |
| 1-8.P(FAT-SA) 50:50 | A | 7 | 75 | 12 | 80 |
| 1-16.P(FAT-SA-CPP)A 40:50:10 | | 11 | 11 | 120 | 15 | 88 |

[a]Films prepared by melt compression (A) or by solvent casting (B).

Modifications and variations of the present invention will be obvious to those skilled in the art from the foregoing detailed description. Such modifications and variations are intended to come within the scope of the appended claims.

I claim:

1. A polyanhydride polymerized from monomers of the group consisting of dimers and trimers of unsaturated fatty acids and dimers and trimers of non-naturally occurring unsaturated aliphatic acids.

2. The polyanhydride of claim 1 wherein the monomer is selected from the group consisting of dimers and trimers of naturally occurring unsaturated fatty acids.

3. The polyanhydride of claim 2, wherein the monomer is selected from the group consisting of dimers and trimers of oleic, erucic, lauroleic, myristoleic, gadoleic, ricinoleic, palmitoleic, linoleic, linolenic, and arachidonic acids.

4. The polyanhydride of claim 1, wherein the monomer is selected from the group consisting of dimers and trimers of non-naturally occurring unsaturated aliphatic acids.

5. The polyanhydride of claim 4, wherein the monomer is selected from the group consisting of dimers and trimers of acrylic, methacrylic, fumaric, crotonic, vinyl acetic (3-butenoic), isocrotonic, allylacetic (4-pentenoic), hexenoic and undecylenic acids.

6. The polyanhydride of claim I comprising an aliphatic dicarboxylic acid selected from the group consisting of sebacic acid, isophthalic acid, adipic acid, 1,10-dodecanoic acid, or 1,3 bis(p-carboxyphenoxypropane).

7. The polyanhydride of claim 1 that is soluble in organic solvents.

8. The polyanhydride of claim 1 that has a melting point below 65° C.

9. The polyanhydride of claim 1 that is strong and flexible.

10. The polyanhydride of claim 1 prepared by melt polycondensation.

11. The polyanhydride of claim 1 prepared by solution polymerization.

12. The polyanhydride of claim prepared by solvent casting.

13. The polyanhydride of claim 1 prepared by melt casting.

* * * * *